United States Patent
Poganski

(10) Patent No.: US 12,296,156 B2
(45) Date of Patent: May 13, 2025

(54) PEN NEEDLE WITH RETRACTABLE SHIELD

(71) Applicant: Embecta Corp., Andover, MA (US)

(72) Inventor: David Poganski, Midland Park, NJ (US)

(73) Assignee: Embecta Corp., Andover, MA (US)

( * ) Notice: Subject to any disclaimer, the term of this patent is extended or adjusted under 35 U.S.C. 154(b) by 686 days.

(21) Appl. No.: 17/640,139

(22) PCT Filed: Aug. 27, 2020

(86) PCT No.: PCT/US2020/048084
§ 371 (c)(1),
(2) Date: Mar. 3, 2022

(87) PCT Pub. No.: WO2021/045950
PCT Pub. Date: Mar. 11, 2021

(65) Prior Publication Data
US 2022/0331527 A1    Oct. 20, 2022

Related U.S. Application Data

(60) Provisional application No. 62/896,860, filed on Sep. 6, 2019.

(51) Int. Cl.
*A61M 5/32*      (2006.01)
*A61M 5/34*      (2006.01)
(Continued)

(52) U.S. Cl.
CPC ............ *A61M 5/50* (2013.01); *A61M 5/3202* (2013.01); *A61M 5/3213* (2013.01); *A61M 5/34* (2013.01);
(Continued)

(58) Field of Classification Search
CPC ............... A61M 5/326; A61M 5/3243; A61M 2005/3267; A61M 2005/3247; A61M 2005/3254
See application file for complete search history.

(56) References Cited

U.S. PATENT DOCUMENTS 7,645,264 B2    1/2010  Marsh et al.
8,052,653 B2 *  11/2011 Gratwohl .............. A61M 5/326
                                                    604/164.08
(Continued)

FOREIGN PATENT DOCUMENTS

WO       2021045950 A1    3/2021

OTHER PUBLICATIONS

European Search Report in EP Application No. 20861615.5 dated Sep. 25, 2023.
(Continued)

*Primary Examiner* — Laura A Bouchelle
(74) *Attorney, Agent, or Firm* — Greenberg Traurig, LLP; Roman Fayerberg; David J. Dykeman

(57) ABSTRACT

A pen needle (30) for a delivery device includes a hub (32) supporting a needle (54) and a distal needle shield (70) that can retract to expose the needle during injection and return to the extended position after use and lock in the extended position to cover the needle. A proximal needle shield (0.102) moves from a retracted position to an extended position with respect to the hub to shield or cover a proximal end of the needle when the needle hub is separated from the delivery device. A spring (130) extends between the distal needle shield and the proximal needle shield to bias each needle shield to the respective extended position. The distal needle shield (70) is coupled to the proximal needle shield (102) in an initial position to retain the spring (130) in a compressed state. The distal needle shield (70) is depressed to disengage the distal needle shield from the proximal
(Continued)

needle shield (102) so that the spring expands to an extended state and moves the shields to the extended positions. A locking member (142, 156) can be provided to lock the proximal needle shield (70) and distal needle shield (102) in the extended position.

26 Claims, 11 Drawing Sheets

(51) Int. Cl.
*A61M 5/46* (2006.01)
*A61M 5/50* (2006.01)

(52) U.S. Cl.
CPC ....... *A61M 5/46* (2013.01); *A61M 2005/3267* (2013.01)

(56) References Cited

U.S. PATENT DOCUMENTS

| | | | |
|---|---|---|---|
| 8,057,444 B2 | 11/2011 | Hartmann et al. | |
| 8,632,503 B2 * | 1/2014 | Ruan | A61M 5/326 |
| | | | 604/198 |
| 8,801,673 B2 * | 8/2014 | Zaiken | A61M 5/3257 |
| | | | 604/206 |
| 2001/0031949 A1 | 10/2001 | Asbaghi | |
| 2009/0069755 A1 | 3/2009 | Horvath | |
| 2009/0254042 A1 | 10/2009 | Gratwohl et al. | |
| 2012/0022460 A1 | 1/2012 | Horvath et al. | |

OTHER PUBLICATIONS

International Search Report dated Nov. 20, 2020, which issued in the corresponding PCT Patent Application No. PCT/US2020/048084.

* cited by examiner

PEN NEEDLE WITH RETRACTABLE SHIELD

This application claims priority to U.S. Provisional Patent Application No. 62/896,860, filed on Sep. 6, 2019, which is hereby incorporated by reference in its entirety.

BACKGROUND

Field of the Disclosure

The disclosure is directed to a pen needle adapted for attachment to a medication delivery device, such as a medication delivery pen. The pen needle in one embodiment has a needle hub with at least one retractable needle shield where the needle shield can be retracted during use and extended after use to shield or cover the needle attached to the hub. After use of the pen needle, the needle shield can be locked in the extended position to shield at least one end of the needle. The pen needle can include a distal needle shield for shielding the distal patient end of the needle after use and a proximal needle shield for covering the proximal non-patient end of the needle after separation from the delivery device.

Description of the Related Art

Pen needles are used to attach to a medication pen and are especially useful for delivering self-administered injectable medications such as insulin. In one known commercial device, a needle-bearing hub is provided inside a funnel-shaped outer cover, sometimes referred to as the "outer shield," or simply as the "cover." The cannula or needle is affixed in an axial bore of the hub with one end protruding from the distal or "patient side" of the hub for injecting the patient and the other end of the needle is recessed in a cavity on the proximal or "non-patient" side of the hub, and is adapted for attachment to the medication pen. A paper and foil "teardrop" label is heat sealed on the edge of the open end of the funnel shaped outer cover. In addition, the medication pen may have a cap received over the distal end of the medication pen where the pen needle is installed. To install the pen needle on a medication pen, the user removes the medication pen cap. The user then removes the label on the pen needle outer cover and holds the outer cover to install the hub, typically threading the hub onto the pen. Once the hub is installed on the medication pen, the outer cover can be removed by pulling the outer cover distally off the hub. A separate inner needle shield sits over the needle, which the user must remove to administer an injection. The inner shield generally sits on the hub and simply helps the user locate the needle without forming a sterility barrier. After use, the user may use the outer cover to unthread the hub from the pen and dispose of the pen needle.

Medication pens and associated pen needles are disclosed in U.S. Pat. No. 7,645,264, and U.S. Patent Application Publication Nos. 2009/0069755 and 2012/0022460, all of which are incorporated by reference in their entirety for their teachings of pen needle design and construction. A device for arranging a releasable pen needle on an injection pen and releasing the pen needle into a mating storage or disposal container is disclosed in U.S. Pat. No. 8,057,444, also incorporated by reference for this teaching.

Pen needles can include a cover or shield to cover the end of the needle to prevent re-use and accidental needle stick. Pen needles are also known that have a shield to cover the proximal end of the needle when the pen needle is separated from the delivery device. While the prior devices are generally suitable for the intended use, there is a need in the industry for improvements to the pen needles.

SUMMARY

A pen needle is provided for use with a medication delivery device, such as a delivery pen, for injecting a medication into a patient. The pen needle in one embodiment has a hub with a cannula or needle and a distal needle shield that can retract during use to expose the needle during use and to extend to cover the distal end of the needle after use. In one embodiment, the needle shield can have a locking mechanism to lock the distal needle shield in the extended position and prevent re-use. One feature of the pen needle is a retractable distal needle shield that can retract during use to expose the needle and slide to an extended position after use to cover the needle, and a proximal needle shield coupled to the distal needle shield when the distal needle shield is in an extended position and the proximal needle shield is in a retracted position. A biasing member, such as spring, is included to bias the distal needle shield and proximal needle shield to the respective extended position.

The pen needle is able to attach to a delivery pen or other delivery device where the pen needle includes a proximal needle shield that can lock in place after use to cover the non-patient end of the needle. The proximal needle shield for the non-patient end is in a retracted position before use and moves to an extended position after separation from the delivery device to cover the non-patient proximal end of the needle in the needle hub to inhibit re-use.

The pen needle in one embodiment includes a hub supporting a needle or cannula. A removable cover can fit over the end of the hub to cover the pen needle during storage until ready for use. A movable distal needle shield is coupled to the hub that can retract during use to expose the patient end of the needle and can be deployed by moving or sliding outwardly after use to cover the patient end of the needle and prevent further use or accidental needle stick. A proximal needle shield is coupled to the hub and moves to shield the proximal, non-patient end of the needle. A biasing member, such as a spring member, can be positioned between the distal needle shield and the proximal needle shield to bias the needle shields outwardly in a distal direction.

In one embodiment, a proximal needle shield is coupled to the distal needle shield when the needle shields are in an initial position before use. A coupling member couples the distal needle shield to the proximal needle shield where the coupling member can disengage to separate the distal needle shield from the proximal needle shield to deploy the shields to the extended position. A biasing member is provided within the hub for biasing the distal needle shield outwardly to the extended position covering the distal end of the needle and for biasing the second proximal needle shield outwardly to cover the proximal end of the needle. In one embodiment, a single spring member biases the distal needle shield and the proximal needle shield to the respective extended position.

In one embodiment, the pen needle includes a hub having a distal needle shield that can slide relative to the hub between a first extended position to cover the distal end of the needle and a retracted position to expose the distal end of the needle. A proximal needle shield is provided in the pen needle and coupled to the distal needle shield. The distal needle shield disconnects from the proximal needle shield by axial movement of the distal needle shield toward the proximal end of the hub. In one embodiment, the distal needle shield rotates by the axial movement to separate from the proximal needle shield where a biasing member slides the proximal needle shield to an extended position and biases the distal needle shield to the extended position.

In one embodiment, a pen needle has a hub with a needle having a distal end extending from the distal end of the hub and a proximal end at a proximal end of the hub. A distal needle shield is movable with respect to the hub between a first extended position to cover the needle and a retracted position to expose the needle. The distal needle shield is biased to a second extended position. A proximal needle shield is biased from a retracted position to an extended position to cover the proximal end of the needle when the pen needle is separated from the delivery device. A spring has a distal end engaging the distal needle shield to bias the distal needle shield to the extended position and a proximal end to bias the proximal needle shield to the extended position.

The first distal needle shield in one embodiment can include one or more flexible coupling tabs that engage complementing tabs on the proximal needle shield. During use the distal needle shield rotates when retracted where the tabs separate from the tabs of the proximal needle shield so that a spring can bias the distal needle shield and proximal needle shield to the respective extended positions.

The pen needle includes a hub having a proximal end for attachment to a delivery device and a distal end. A needle is coupled to the hub and has a distal end extending from the distal end of the hub. A distal needle shield is coupled to the hub for sliding between an extended position shielding the distal end of the needle and a retracted position to expose the distal end of the needle. A proximal needle shield is coupled to the hub and to the distal needle shield. The distal needle shield is rotatable from a first angular position to a second angular position when the needled shield moves toward the proximal end to separate the distal needle shield from the proximal needle shield.

The features of the pen needle include a hub having a needle coupled to the hub and having a distal end extending from the distal end of the hub and a proximal end for connecting to a delivery device. A distal needle shield is coupled to the hub for sliding between a first extended position to shield the distal end of said needle, a retracted position to expose the distal end of said needle for injecting a substance into a patient, and a second extended position to shield the distal end of the needle. A proximal needle shield is coupled to the hub for sliding from a retracted position where the proximal end of said needle is exposed to an extended position. The proximal needle shield is coupled to the distal needle shield in the retracted position. The distal needle shield is rotatable by axial movement relative to the hub from a first position to a second position to disconnect the distal needle shield from the proximal needle shield.

A method of using the pen needle, such as for injecting a substance into a patient, is also provided. The method retracts the needle shield from a first extended position to a retracted position to expose the needle and disengage from a proximal needle shield. The distal needle shield then moves to a second extended position to shield the needle to lock the needle shield in the extended position. The proximal needle shield moves to an extended position to shield the proximal end of the needle.

A pen needle comprises a hub having a distal end, and a proximal end for attachment to a delivery device, a needle coupled to the hub and having a distal end extending from the distal end of said hub. A distal needle shield is coupled to the hub and slidable between a first extended position to cover the distal end of the needle and a retracted position to expose the distal end of the needle for injecting a substance into a patient, and a second extended position to shield the distal end of said needle.

In another embodiment, a pen needle comprises a hub having a side wall, a proximal end for attachment to a delivery device, and a distal end. A needle is coupled to the hub and has a distal end extending from the distal end of the hub and a proximal end at a proximal end of the hub. A needle is coupled to the hub and has a distal end extending from the distal end of the hub and a proximal end at a proximal end of said hub. A distal needle shield is coupled to the hub for sliding with respect to the hub between a first extended position to cover the distal end of the needle, a retracted position to expose the distal end of the needle, and a second extended position to cover the distal end of the needle. The distal needle shield has a first coupling member. A proximal needle shield is included at the proximal end of the hub and has a base on a distal side of inner wall, and a projection extending toward the proximal end of said hub through an opening in the inner wall of the hub. The proximal needle shield is movable from a retracted position where the proximal end of the needle is exposed and an extended position relative to the proximal end of the needle. The proximal needle shield has a second coupling member configured for coupling to the first coupling member of the distal needle shield. A spring has a first end contacting the distal needle shield for biasing the distal needle shield in a distal direction to the second extended position, and a second end contacting the base of said proximal needle shield for biasing the proximal needle shield and the projection in a proximal direction to the extended position.

These and other aspects and features of the pen needle will be apparent from the following detailed description of the invention and the drawings.

BRIEF DESCRIPTION OF THE DRAWINGS

The following is a brief description of the drawings, in which.

Figure 1:
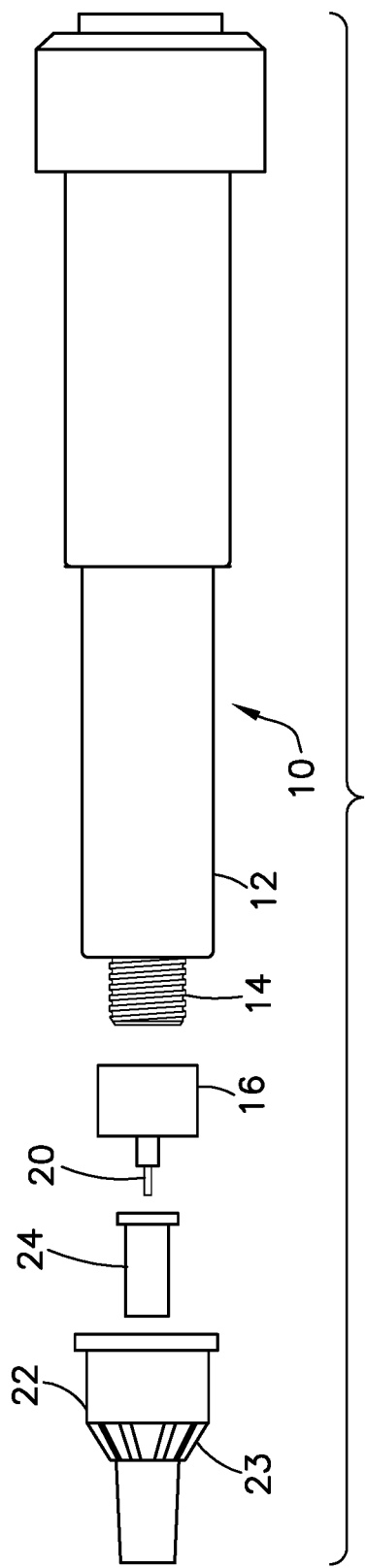
FIG. 1 is a side elevational view of the pen needle and delivery pen device.

The figures are not to scale, and some features are omitted in certain views to better illustrate other features.

DETAILED DESCRIPTION

As used herein, the "distal" direction is in the direction of the injection site, and the "proximal direction" is the opposite direction. The "axial" direction is along the longitudinal axis of the device. The needle cannula is generally arranged axially in the device. "Radially" is a direction perpendicular to the axial direction. Thus, "radially inward" generally means closer to the axis of the needle. "Circumferentially" refers to arranging around the circumference, so that threads are arranged circumferentially on the end of a threaded fitting. The "top" view of a pen needle is looking at the pointed end of the needle. A medication delivery pen or delivery device is used herein to refer to a device having a medication compartment, typically containing multiple doses of medication, and a separate pen needle. The phrase "pen needle" refers to a needle-bearing assembly which can be attached to the medication delivery pen body so that a proximal end of the pen needle assembly accesses a medication compartment and a distal end is adapted for insertion into an injection site to perform one or more injections. The terms "needle" and "cannula" are used herein interchangeably to refer to a thin tubular member having a sharpened end for insertion into an injection site on a subject. The needle or cannula has a lumen for delivery and injection of a medication to the patient.

The different features of the embodiments can be used in combination with and used with other embodiments as long as the combined parts are not inconsistent with or interfere with the operation of the device and assembly. This disclosure is not limited in its application to the details of construction and the arrangement of components set forth in the following description or illustrated in the drawings. The embodiments herein are capable of being modified, practiced or carried out in various ways. The phraseology and terminology used herein is for the purpose of description and should not be regarded as limiting. The use of "including," "comprising." or "having" and variations thereof herein is to encompass the items listed thereafter and equivalents thereof as well as additional items. Unless limited otherwise, the terms "connected," "coupled," and "mounted," and variations thereof herein are used broadly and encompass direct and indirect connections, couplings, and mountings. In addition, the terms "connected" and "coupled" and variations thereof are not limited to physical or mechanical connections or couplings. Further, terms such as up, down, bottom, and top are relative, and are to aid illustration, but are not limiting. The embodiments are not intended to be mutually exclusive so that the features of one embodiment can be combined with other embodiments as long as they do not contradict each other. Terms of degree, such as "substantially", "about" and "approximately" are understood by those skilled in the art to refer to reasonable ranges around and including the given value and ranges outside the given value, for example, general tolerances associated with manufacturing, assembly, and use of the embodiments. The term "substantially" when referring to a structure or characteristic includes the characteristic that is mostly or entirely present in the structure.

In one embodiment, the delivery device is a pen needle delivery device 10, as shown in FIG. 1, which typically comprises a dose knob/button, an outer sleeve 12, a threaded end 14 for coupling to a pen needle 18, and a cap. A dose knob/button allows a user to set the dosage of medication to be injected. The outer sleeve 12 is gripped by the user when injecting medication. A cap is used by the user to securely hold the pen needle device 10 in a shirt pocket or other suitable location and provide cover/protection from accidental needle injury.

Figure 2:
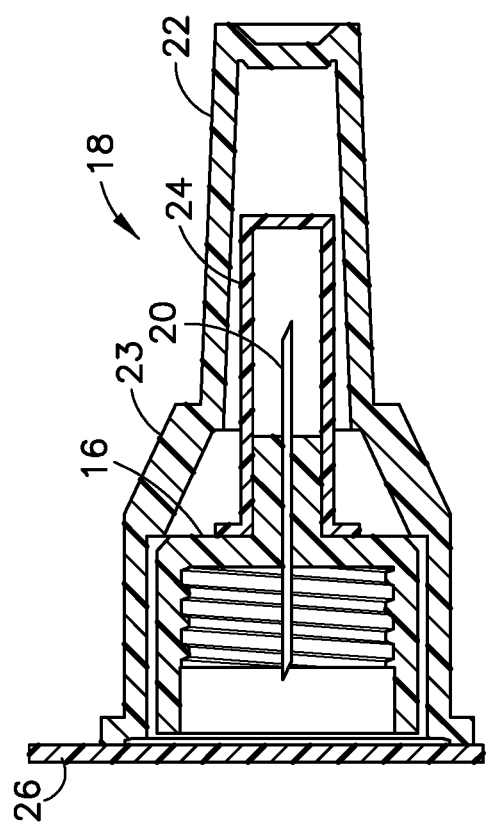
FIG. 2 is a cross sectional side view of the pen needle of FIG. 1.

In standard pen needle devices the dosing and delivery mechanisms are found within the outer sleeve 12 and is not described in greater detail here as they are understood by those knowledgeable of the art. A medicament cartridge is typically attached to a standard pen injector housing by known attachment mechanism. The distal movement of a plunger or stopper within the medicament cartridge causes medication to be forced into the reservoir housing. The medicament cartridge is sealed by a septum and punctured by a septum penetrating needle cannula located within a reservoir or housing. Reservoir housing is preferably screwed onto the medicament cartridge although other attachment mechanism can be used. The pen needle delivery device can be a standard pen delivery device known in the industry so that the pen needle delivery device is not shown in detail. A typical pen needle assembly 18 as shown in FIG. 2 includes a needle hub 16 supporting a cannula 20, an outer cover 22 having ribs 23, and an inner shield 24. A protective seal 26 is attached to the open end of the outer cover as shown in FIG. 2 to enclose the needle hub and cannula to maintain a clean and sterile condition. The seal 26 can be a label or other closure member that can be easily peeled from the outer cover to access the needle hub during use.

Figure 3:
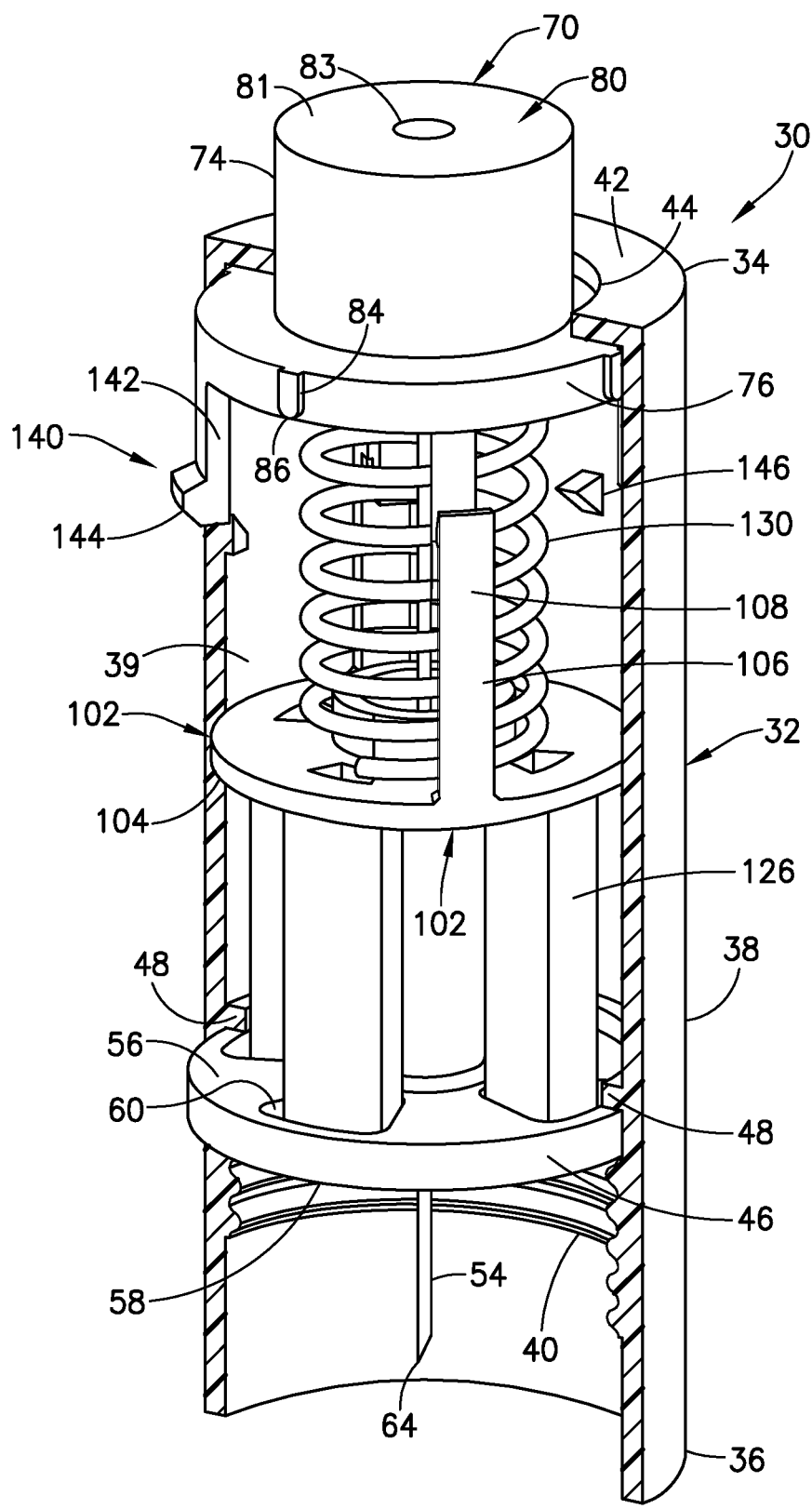
FIG. 3 is a perspective view of a pen needle in partial cross section showing the distal needle shield and proximal needle shield in the initial position.

In the embodiment shown in FIG. 3, the pen needle 30 includes the hub 32, a distal needle shield 70, a proximal needle shield 102, and a spring 130 for biasing the needle shields. The hub 32 has a distal end 34 for contacting the patient and a proximal end 36 for connecting to the delivery pen. The hub 32 can be a one-piece unit or made from separate components that are coupled together. In the embodiment shown, the hub 32 has a sidewall 38 with a substantially cylindrical configuration. The open proximal end 36 has a shape and configuration for coupling to the delivery pen 10 or other delivery device. In the embodiment shown, internal threads 40 are provided at the proximal end of the sidewall for connecting to the delivery device in a known manner. The pen needle 30 is configured for delivering a substance to a patient, such as insulin or other medication. In one embodiment, the pen needle and delivery pen are configured for delivering a controlled dose of insulin to a patient.

The distal end of the sidewall 38 forming the hub 32 has an end wall 42 with an opening 44 forming an open distal end of the hub 32. The opening 44 has a dimension less than the diameter of the sidewall 38. An inner wall 46 is positioned in the interior cavity of the hub 32 defined by the sidewall 38 and extends in a plane substantially perpendicular to the longitudinal axis of the hub 30 and the sidewall 38. The inner wall is fixed relative to the sidewall 38 during use of the pen needle. The inner wall 46 extends between the opposite sides of the side wall and is coupled to the side wall by a suitable coupling mechanism. As shown in FIG. 3, the inner wall 46 is spaced inwardly from the distal end and spaced inwardly from the proximal end of the sidewall to form a cavity on each side of the inner wall 46. The inner wall defines the bottom of the distal cavity at the distal end of the sidewall and a proximal cavity at the open proximal end 36. In the embodiment shown, the inner wall 46 is received between two spaced apart radial ribs 48 extending radially inward from the sidewall 38 to form a recess between the ribs having a dimension to receive and capture the inner wall 46. In other embodiments, the inner wall can be attached by an adhesive, thermal bonding or welding. In the embodiment shown, the inner wall 46 is separate member although the inner wall 46 can be integrally formed or molded with the side wall as single one-piece unit.

Figure 4:
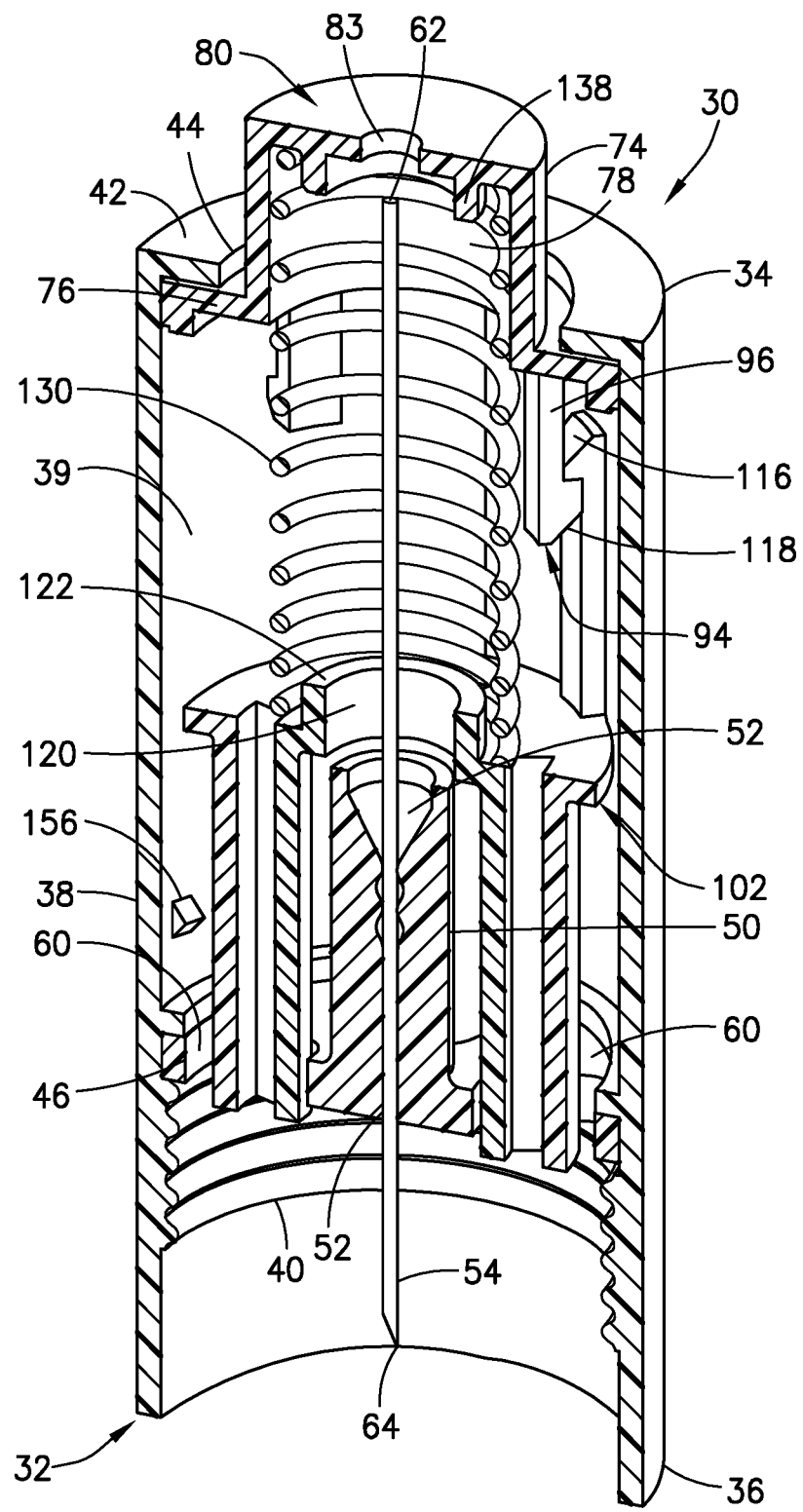
FIG. 4 is a cross sectional view of the pen needle of FIG. 3.
Figure 5:
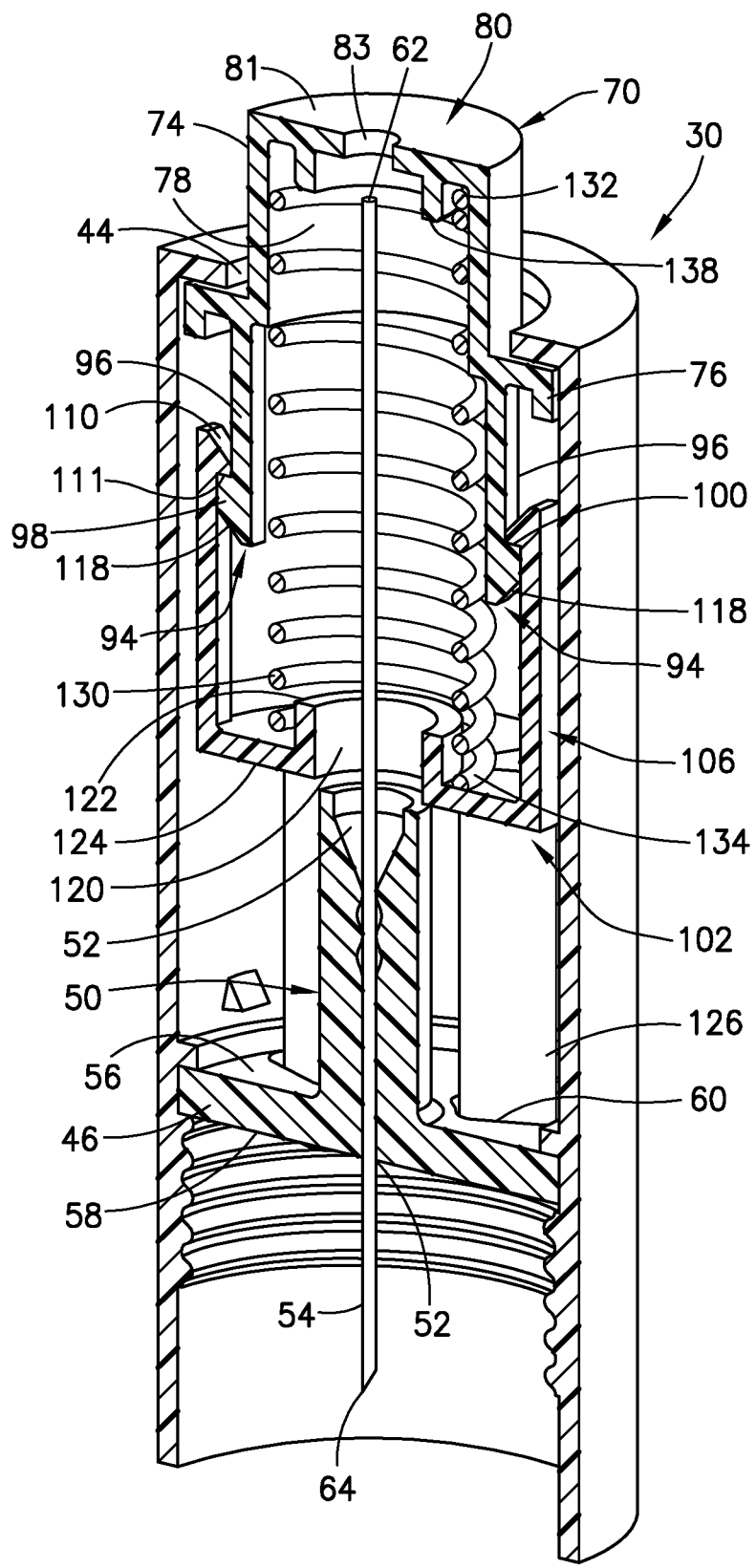
FIG. 5 is a cross sectional view of the pen needle showing the coupling members of distal needle shield and proximal needle shield.

As shown in FIGS. 4 and 5, the inner wall 46 has a center post 50 extending in a distal direction with an axial passage 52 supporting a needle 54. The post 50 extends from a distal side surface 56 of the inner wall 46 opposite a proximal surface 58 of the inner wall. The post 50 extends axially toward the distal end of the hub 32 and into a distal cavity formed by the sidewall 38. The axial passage 52 has a dimension to receive and support the needle 54 by use of an adhesive as known in the art. The inner wall 46 includes openings 60 spaced around the center post 50 where the openings extend through the inner wall between the distal face 56 and the proximal face 58. In other embodiments, the inner wall can have a single opening.

Needle 54 is generally a hollow needle, such as a steel needle, with a sharpened tip at a distal end 62. The distal or patient end of the needle has a gauge and length for penetrating the skin to a desired depth and for delivery of a medication to a patient. A proximal end 64 at the proximal end of the hub 30 is positioned for piercing a septum in a delivery device for receiving the drug or medication from the delivery device in a usual manner. The distal end 62 can have an exposed length extending from the distal end of sidewall 38 and the hub during the injection of about 3-10 mm and typically about 4-6 mm. The needle can have a gauge ranging from 32 gauge to 36 gauge. The proximal end 64 of the needle has a length to extend toward the proximal end of the hub a length to pierce the septum of the delivery pen to provide a fluid connection between the delivery pen and the needle 54.

Referring to FIGS. 3-6, the pen needle 30 includes the distal needle shield 70 and the proximal needle shield 102 for movement relative to the hub 32 and the needle 54. The distal needle shield 70 forms a shield or cover for the distal end 62 of the needle 54 to prevent re-use of the pen needle after use and to prevent inadvertent needle stick before and after use. The distal needle shield 70 in the embodiment shown is configured for sliding within the sidewall 38 and the opening 44 in the end wall 42 of the hub 32. The distal needle shield slides between an extended position shown in FIG. 3 and a retracted position shown in FIG. 7 to expose the needle 54 for injecting a patient.

In the embodiment shown, the distal needle shield 70 is configured to slide relative to the sidewall 38 and the open distal end of the sidewall 38 of the hub 32. The distal needle shield 70 has a main body 74 projecting through the opening 44 in the end wall 42 of the hub 32. The main body 74 in the embodiment shown has a substantially cylindrical configuration. A radially extending flange 76 extends outwardly from the main body 74 and has a configuration to slide in the interior of the sidewall 38. The flange 76 has a distal surface to contact the end wall 42 to limit distal movement of the distal shield 70 and capture the distal needle shield 70 within the sidewall 38 of the hub 32. The main body 74 of the distal shield 70 has an axial passage 78 and an axial length to retract a distance to expose the distal end of the needle 54 for injecting the patient and a length to shield and cover the distal end of the needle 54 when moved to the extended position shown in FIG. 3. The main body 74 of the distal needle shield 70 has an end wall 80 with an outer distal surface 81 forming a skin contact surface. The main body 74 has a width less than a radial width of the flange 76 whereby the body 74 can slide in the opening 44. The distal surface 81 and the end wall are shown as a flat surface having an opening 83 to allow the needle 54 to pass though during an injection. In other embodiments, the surfaces can have a convex shape to control the depth of penetration of the needle into the skin. The distal needle shield 70 has a dimension to shield and cover the needle in a manner to prevent the user from contacting the needle tip.

Figure 8:
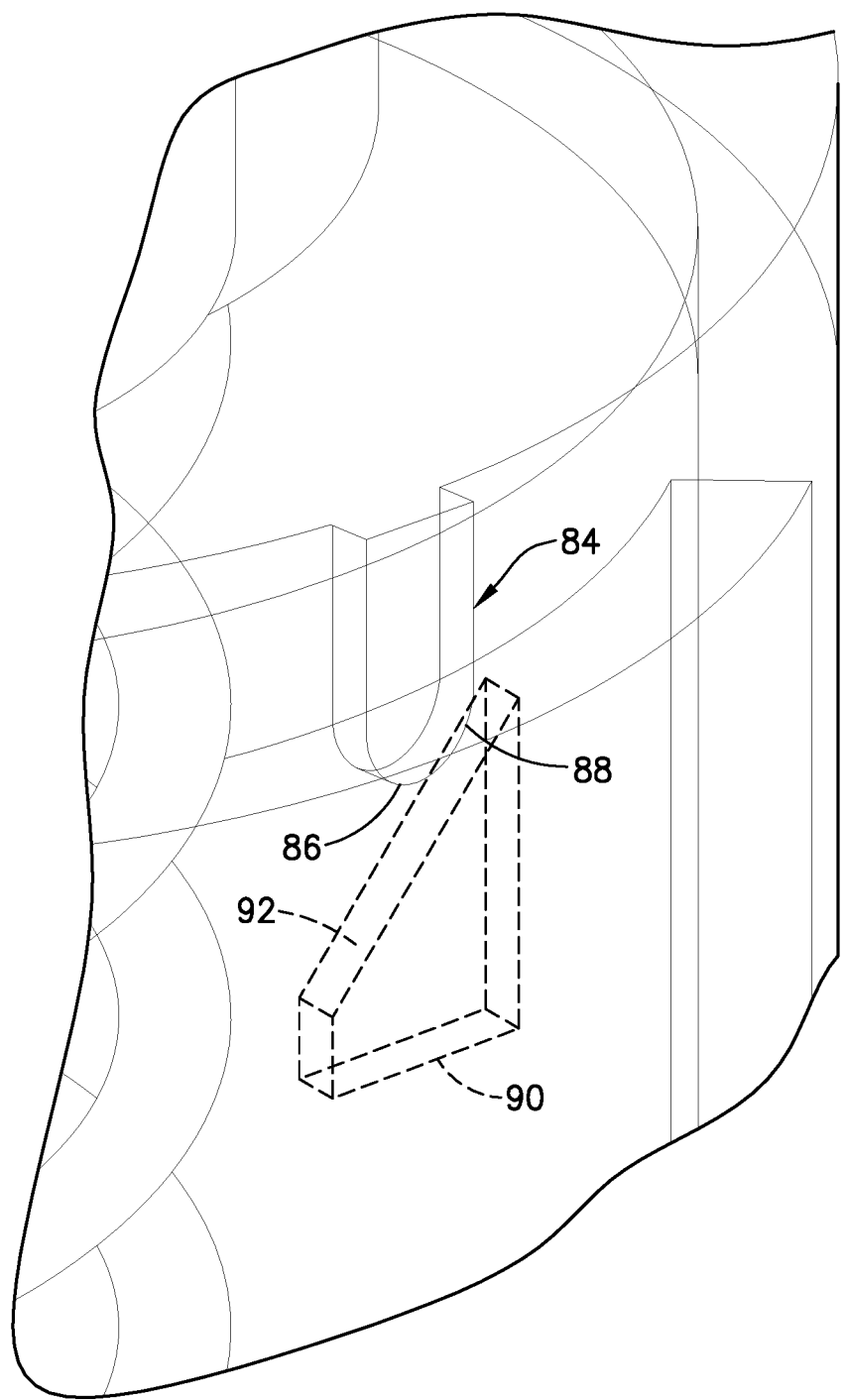
FIG. 8 is a schematic view of the detents on the distal needle shield and the hub.

The flange 76 has a radial surface 82 with a rotation member shown as a detent or projection 84. In the embodiment shown a plurality of spaced apart projections 84 are provided on the flange. The projections 84 in the embodiment shown project radially outward from the radial surface 82. The projections 84 have a proximal end 86 with a curved surface having a convex shape. The curved surface forms a surface that is inclined with respect to a longitudinal dimension of the distal shield and is inclined relative the direction of axial movement in the distal shield within the hub 32. The projections 84 have a leading face 88 oriented at an incline relative to the longitudinal axis of the hub 32. The inner surface 39 of the sidewall 38 of the hub 32 has complementing rotation members shown as detents 90 that cooperate with the projections 84 of the flange 76 as shown in FIG. 8. The detents 90 project inwardly into the axial passage of the sidewall 38 to contact the detents 84 by axial movement of the distal needle shield. The detents 90 have a complementing inclined surface 92 that is inclined relative to the axis of the hub 32. The detents 90 are fixed relative to the sidewall 38 and define a cam surface for rotating the distal needle shield 70 by axial movement of the distal needle shield 70 in a proximal direction.

Figure 7:
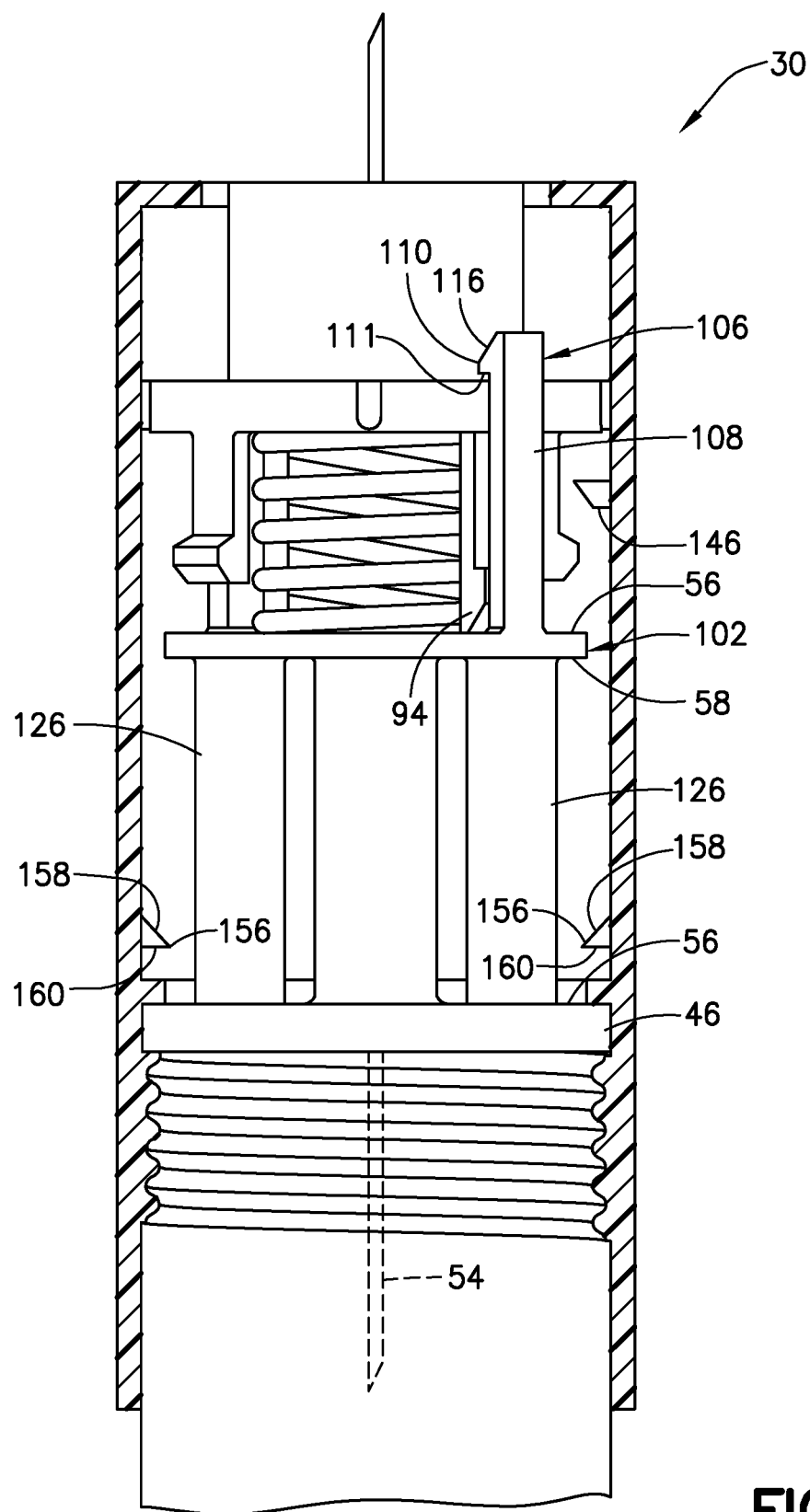
FIG. 7 is a partial cross sectional view showing the pen needle connected to a delivery device and the distal needle shield retracted to expose the needle.

The detents 90 are spaced from the end wall 42 a distance corresponding to the position of the projection 84 on the distal needle shield 70 when the distal needle shield 70 is positioned in the extended position with the flange 76 contacting the inner surface of the end wall 42 to cover the needle. The detent 90 contacts the respective projection 84 when the distal needle shield 70 is in the initial position shown in FIG. 3 before use. The detents 90 can contact the projections 84 to hold the distal needle shield 70 in the initial extended position until ready for use. The axial movement of the distal needle shield 70 toward the proximal end of the hub 32 causes the distal needle shield 70 to rotate about the axis of the hub by the surfaces of the projections 84 sliding on the inclined surfaces of the detents 90 until the projections 84 separate from the detents 90. The distal needle shield 70 can then slide toward the proximal end of the hub to expose the distal end of the needle as shown in FIG. 7.

The flange 76 of the distal needle shield 70 includes a coupling member 94. In the embodiment shown, the flange includes two coupling members 94. The coupling member 94, in the embodiment shown, includes an axially extending leg 96 extending proximally with respect to the distal needle shield. A tab 98 projects from the leg and includes an distal face 100 oriented in a plane parallel to a plane of the flange 76 and perpendicular to a central axis of the distal shield. The tab 98 has an inclined proximal face as shown. In one embodiment, the tab 98 projects radially outward.

Figure 6:
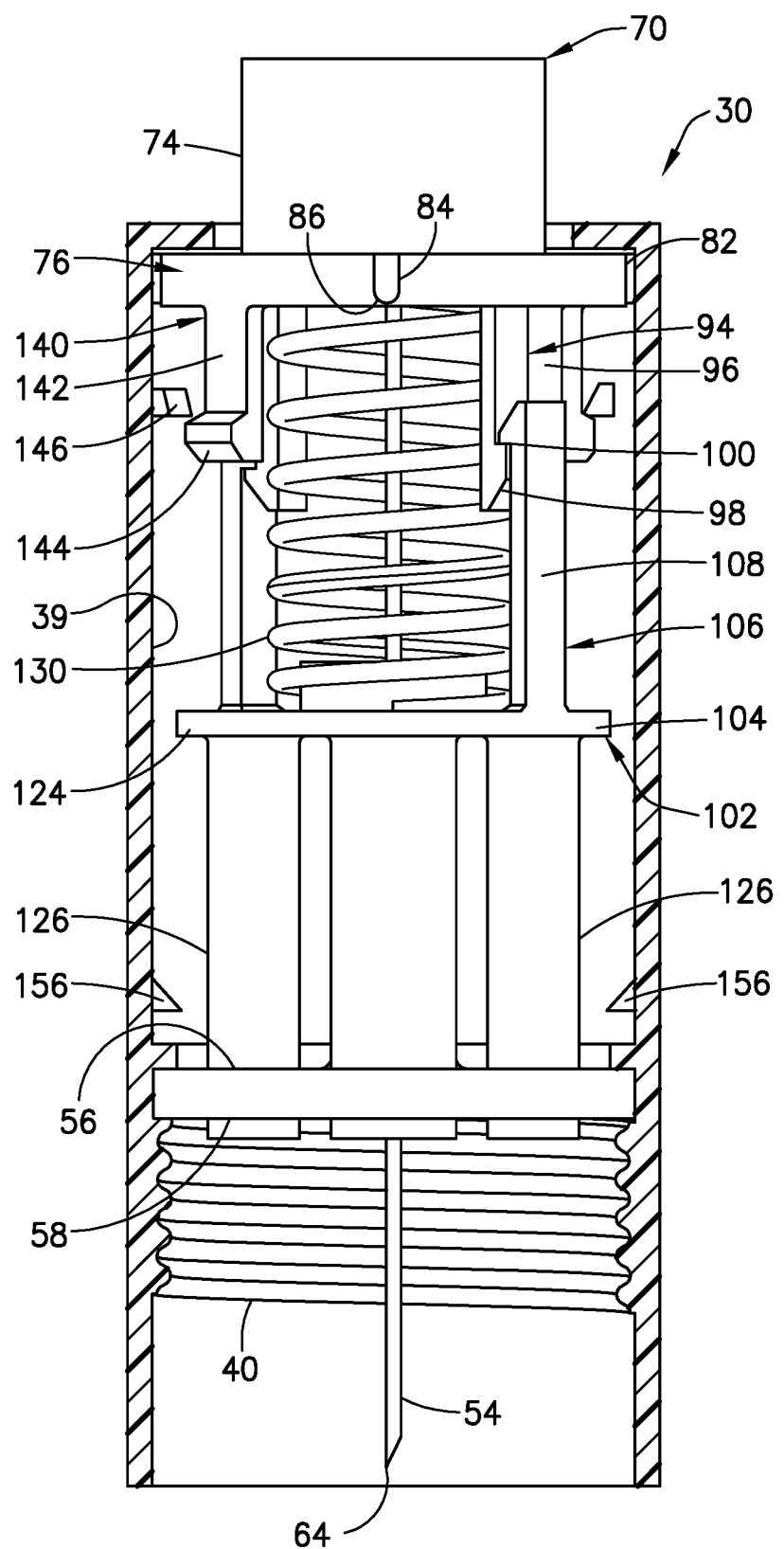
FIG. 6 is partial cross sectional view showing the distal needle shield and proximal needle shield.
Figure 9:
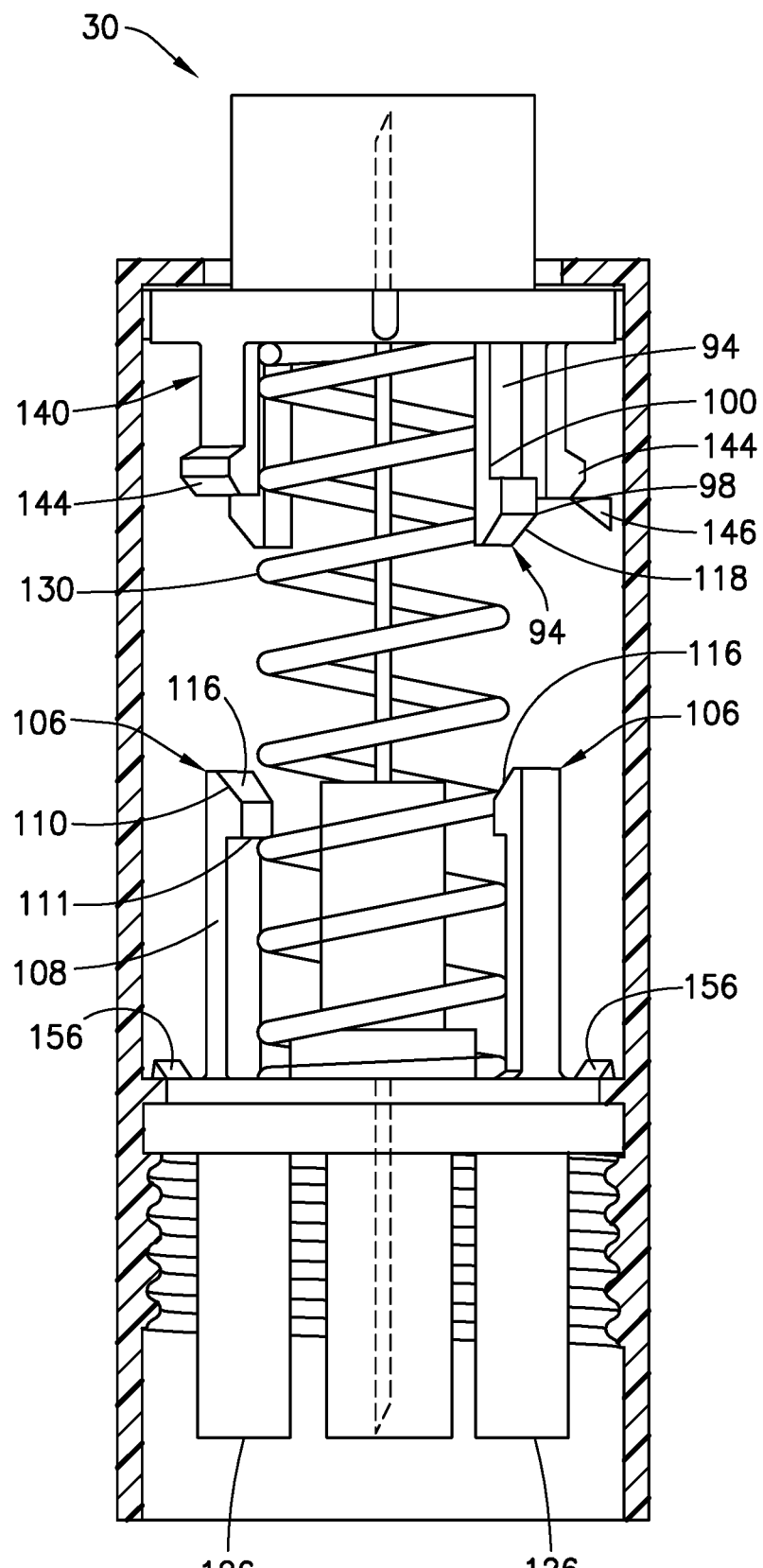
FIG. 9 is a cross sectional view showing the needle shields deployed in the extended and locked position.

The proximal needle shield 102 is positioned within the hub 32 for sliding from a retracted position shown in FIG. 3 to an extended position shown in FIG. 9. The proximal needle shield 102 includes a base 104 oriented on a distal side of the inner wall 46 and spaced between the distal end of the sidewall 38 and the inner wall 46. The base 104 in the embodiment shown has a substantially planar configuration with a circular outer edge complementing the cylindrical inner surface 39 of the sidewall 38. A coupling member 106 extends from the base 104 in a distal direction toward the distal needle shield 70. In the embodiment shown a pair of coupling members 106 are provided for mating with a respective coupling member 94 of the distal needle shield 70. The coupling members 106 include an axially extending leg 108 having a coupling tab 110 at a distal end of the respective leg 108. The tab 110 forms an undercut face 111 oriented in a plane substantially perpendicular to the longitudinal axis of the hub. As shown in FIGS. 5 and 6, the face 111 of tab 110 engages the face 100 of tab 98 and couples the distal needle shield 70 to the proximal needle shield 102. A distal face of the tab 110 in the embodiment shown has an inclined surface 116 that complements an inclined surface 118 of the tab 98 to allow the tabs to slide past each other during assembly. The coupling members 94 and 106 are shown as interlocking coupling tabs. Other coupling mechanisms can be used that are able to connect and release the distal needle shield and the proximal needle shield.

The base 104 of the proximal needle shield 70 has a central opening 120 with a dimension for sliding on the post 50. In the embodiment shown, the base 104 has an annular collar 122 extending in a distal direction around the opening 120 for guiding the base on the post 50.

The base 104 has a proximal side 124 with a shielding member that can pass through the openings 44 in the inner wall 46 to an extended position to shield the proximal end of the needle 54 and limit exposure to the patient. In the embodiment shown, the proximal needle shield 102 includes a plurality of shield members 126 extending axially from the base 104 in a proximal direction relative to the hub 32. In the embodiment shown, four shield members 126 are provided although the number of shield members can vary to provide adequate protection from needle stick by the proximal end of the needle 54. The shield members 126 are spaced around the central opening 120 in the base 104 to encircle the proximal end of the needle 54 when moved to the deployed position to limit contact by the user with the needle as shown in FIG. 8. Each shield member 126 is aligned with a respective opening 60 formed in the inner wall 46 to enable the shield members 126 to pass through to encircle the proximal end of the needle 54. The shield members 126 are deployed after use of the pen needle and after the pen needle is separated from the delivery pen. The proximal needle shield 102 can lock in the deployed extended position by locking members 156 on the sidewall where the shield members 126 block the open end of the hub and block access to the internal threads of the hub to prevent the needle hub from attaching to a delivery pen.

A biasing member is included for biasing the distal needle shield 70 and the proximal needle shield 102 axially to the respective extended position. In the embodiment shown, the biasing member is a spring 130 positioned within the sidewall 38 of the hub 32 for biasing the needle shield 70 and the proximal needle shield 102 outwardly in the axial direction to the respective extended positions. As shown in FIGS. 3-6 and 8, the spring 130 has a first end 132 engaging the distal needle shield 70 and a second end 134 engaging the proximal needle shield 102. The inner surface of the end wall 42 of the distal needle shield 70 includes an annular collar 138 for stabilizing the distal end of the spring 130. The spring 130 is shown as a coil spring extending between the distal needle shield 70 and proximal shield 102 and surrounding the needle 54, although other biasing members can be used for biasing the needle shields to the extended position. In alternative embodiments, separate biasing members can be used to bias the distal needle shield and the proximal needle shield. A single spring is used in the illustrated embodiment to simplify construction and reduce the number of parts.

Referring to FIG. 8, the inner surface of the sidewall 38 includes the detents 90 forming an inclined cam surface that is at an incline with respect to the longitudinal axis of the sleeve. The surface 92 is formed at an incline with respect to the axis of the hub 32 and oriented to engage the inclined surface 86 of the projection 84. As shown in FIG. 7, the projection on the needle shield 70 engages the surface 92 whereby moving the needle shield 70 axially inward with respect to the sidewall 42 causes the projection 84 to engage the inclined surface and rotate the needle shield 70 about the longitudinal axis of the pen needle. The distal needle shield 70 rotates with respect to the proximal needle shield 102 to separate the coupling tabs 98 of the distal needle shield 70 from the coupling tabs 112 of the proximal needle shield 102 allowing the spring 130 to bias the proximal needle shield toward the proximal end of the hub 32. The shield members 126 have a proximal end positioned in the respective opening 58 to prevent rotational movement of the proximal shield 102 relative to the inner wall 46. In this manner, the proximal shield 102 is rotationally fixed in the hub 32 while allowing axial sliding from a retracted position to an extended position. The distal needle shield 70 is able to rotate about the longitudinal axis of the pen needle 30 and the proximal needle shield 102.

As shown in FIGS. 3, 6 and 8, the distal needle shield 70 includes a locking member 140 for locking the distal needle shield 70 in a fixed position after use. In the embodiment shown, two locking members 140 are provided where each locking member has a flexible leg 142 extending axially from the proximal end of the distal needle shield 70. The leg 142 includes an outwardly extending tab 144. The tab 144 is oriented to mate with a locking member 146 on the inner surface of the sidewall 38 to retain the distal needle shield 70 in the extended position after use as shown in FIG. 9. In the embodiment shown, the locking member 146 on the sidewall 38 is a detent positioned to engage the tab 144. The locking member 146 is shown as a detent projecting radially inward from the sidewall 38 to engage the tab 144 and prevent movement or retracting of the distal needle shield. Alternatively, the locking member can be a recess formed in the sidewall to capture the tab 144.

The recess 146 is spaced axially from the distal end of the sidewall 38 such that when the distal needle shield 70 is in the extended deployed position after use, the distal needle shield will not retract to prevent re-use of the pen needle. The recess 146 is oriented on the inner surface of the sidewall 38 to be spaced circumferentially from the coupling tab 144 when the distal needle shield 70 and the proximal needle shield 102 are coupled together in the initial position as shown in FIG. 3 so that the distal needle shield can retract to expose the distal end of the needle during an injection. When the distal needle shield 70 rotates by the camming surface of the projection 84 and detent 90, the tab 144 axially aligns with the locking tab 144. The tab 144 springs radially outward to engage the locking member 146 to inhibit rotation and axial movement of the distal needle shield 70 and prevent re-use of the pen needle. The detent of the locking member 146 can have spaced apart longitudinally extending ribs to capture the tab 144 to prevent rotation of the distal needle shield relative to the sidewall 38.

During use, the hub 32 is attached to the delivery pen by the threaded connection where the proximal end of the needle 54 pierces the septum of the delivery pen to provide fluid communication with the drug reservoir in the delivery pen. The distal needle shield 70 is in a first extended position shown in FIG. 3 and is pressed against the skin of the patient to retract the needle shield 70 relative to the needle and sidewall 38 to a retracted position shown in FIG. 7 so that the needle 28 pierces the skin of the patient.

As shown in FIG. 8, the detent 84 of the distal needle shield 70 engages the inclined surface 92 of the detent 90 on the inner surface of the sidewall 38 causing rotation of the distal needle shield 70 relative to the proximal needle shield 102 and the sidewall 38. The axial rotation of the proximal needle shield 70 separates the coupling member 94 of the distal needle shield 70 from the coupling member 106 of the proximal needle shield 102 as shown in FIG. 7. The shield members 126 extend through the respective openings 60 in inner wall 46 into engagement with the end of the delivery pen so that the proximal shield 102 remains in the retracted position until the delivery pen is separated from the pen needle. When the delivery pen is separated from the delivery pen, the spring 130 biases the proximal needle shield 102 to the extended position where the shield members 126 pass through the openings in the inner wall to the extended position around the proximal end of the needle as shown in FIG. 9. The base 104 of the proximal needle shield slides over a locking member 156 on the sidewall where the locking members 156 lock the proximal needle shield 102 in the extended deployed position shown in FIG. 9. In the embodiment shown, the locking member 156 on the inner surface 39 of the sidewall 38 are detents having an inclined distal surface 158 and a proximal locking surface 160. The inclined distal surface 158 forms a ratchet-like member that allows the base 104 to slide over each member 156 in the proximal direction and prevent the base 104 from sliding in the distal direction. Retracting the distal needle shield 70 by pressing against the skin of the patient, the projection 84 and detent 90 rotate the distal needle shield to separate the coupling member 94 and 106 and axially align the tab 144 with the locking member 146. When the needle is withdrawn from the patient, the distal needle shield slides axially to the second extended position shown in FIG. 9 where the tabs 144 slide into the respective recess 146 to inhibit axial and rotational movement of the distal needle shield relative to the hub.

Figure 10:
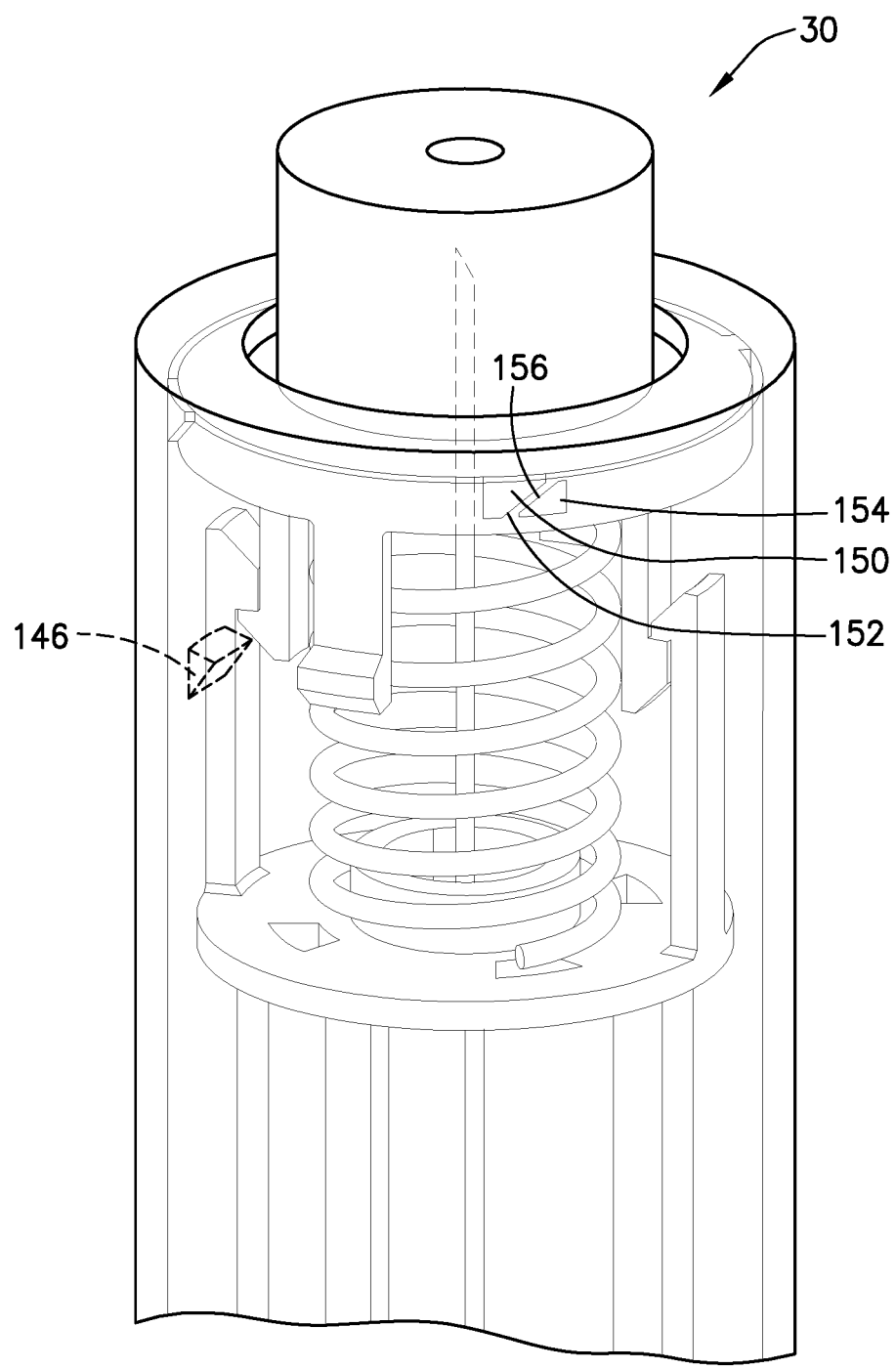
FIG. 10 is a partial perspective view of an alternative embodiment of the pen needle.
Figure 11:
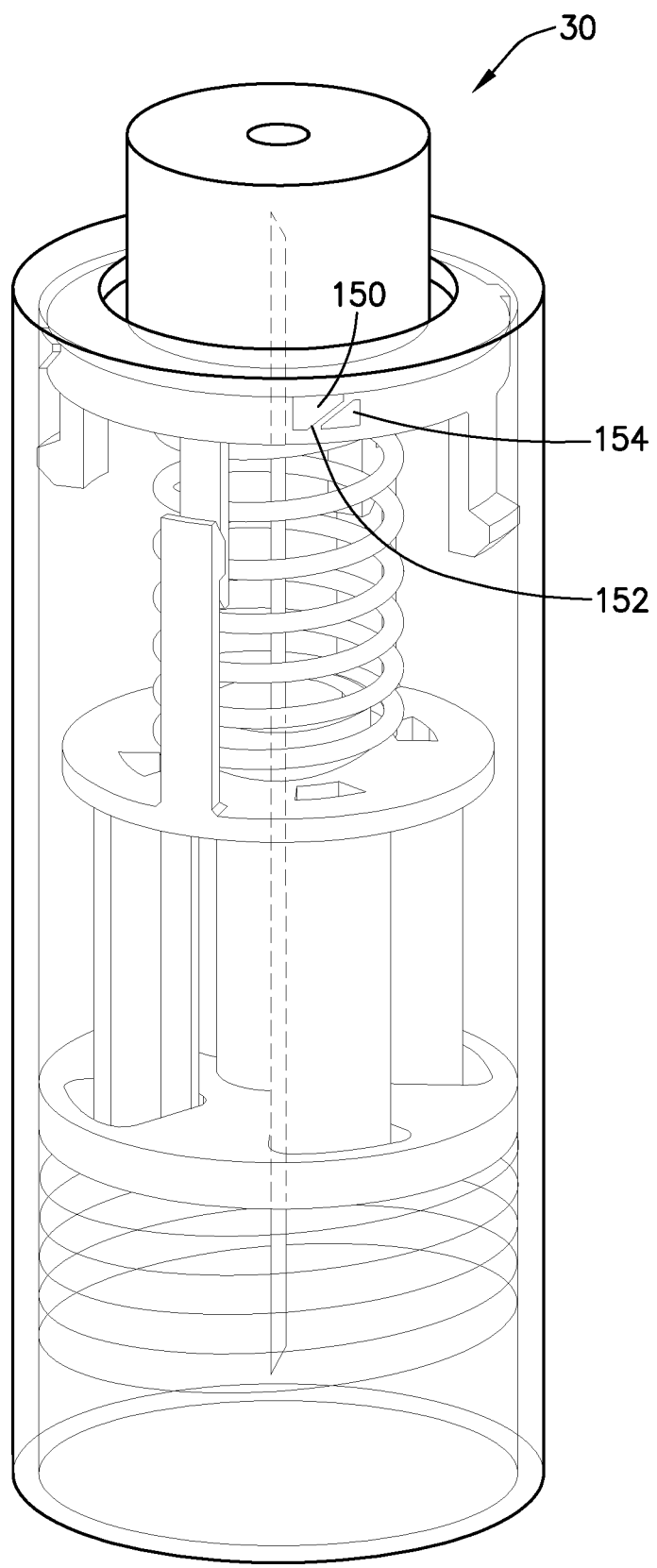
FIG. 11 is a perspective view showing the pen needle of FIG. 10.
Figure 12:
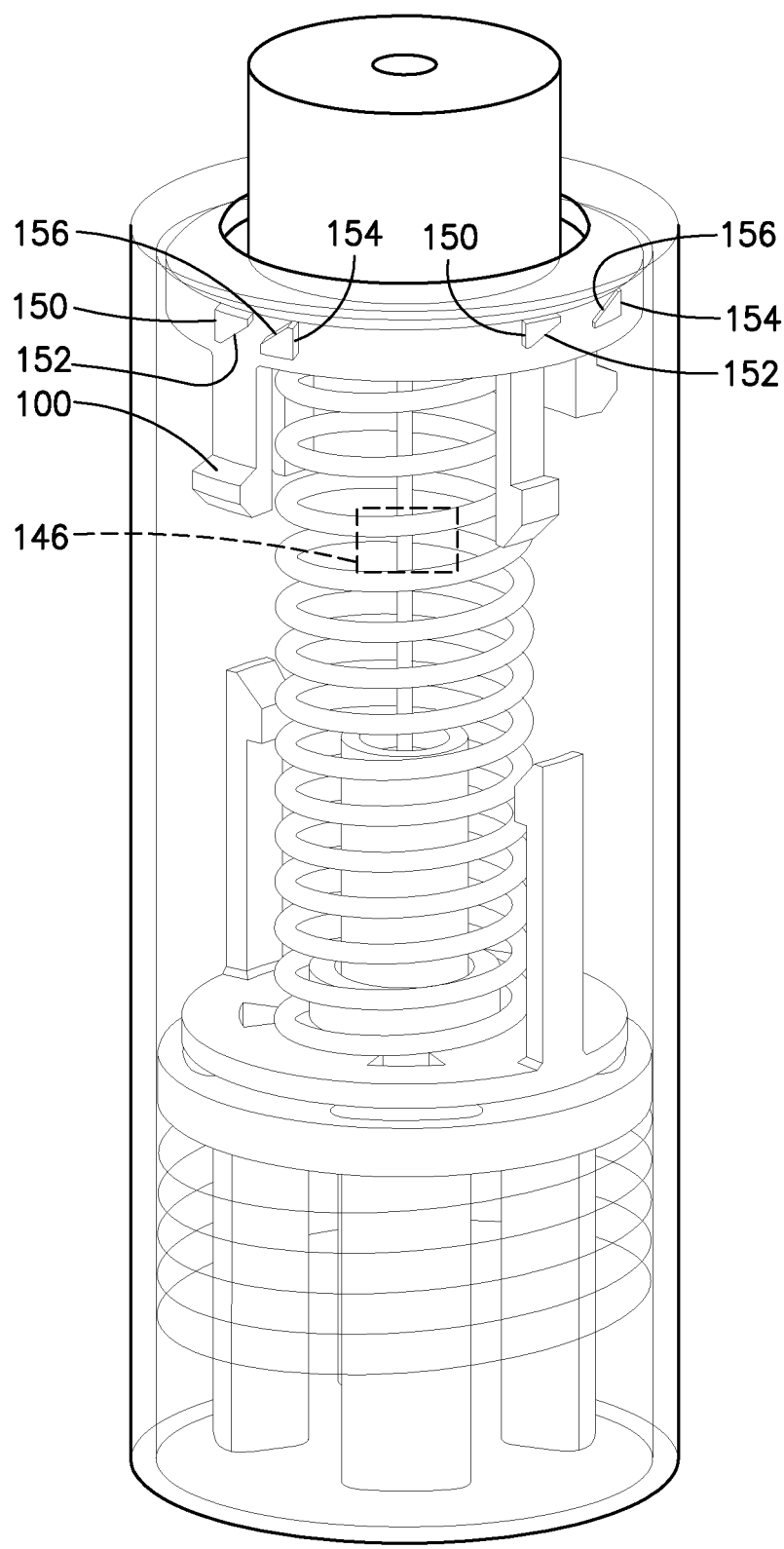
FIG. 12 is a perspective side view of the pen needle of FIG. 10 in the deployed position.

FIGS. 10-12 show an alternative embodiment of the cam mechanism for rotating the distal needle shield 70 relative to the sidewall 38 of the hub 32. In the embodiment shown, the flange 76 of the distal needle shield 70 has a projection 150 extending radially outward where the projection 150 has an inclined surface 152. The inner surface 39 of the sidewall 38 has a similar projection 154 extending radially inward for contacting the projection 150 of the distal needle shield 70. The projection 154 has a similar inclined surface 156 mating with the inclined surface of the distal needle shield when the distal needle shield is in the initial position before use. The contacting inclined surfaces form camming surfaces and cause the distal needle shield 70 to rotate by axial movement of the distal needle shield 70 into the sidewall 38 and separate the coupling members 94 of the distal needle shield from the coupling members 106 of the proximal needle shield.

In the embodiments, the components of the hub and shield are typically injection molded plastic, such as acrylonitrile butadiene styrene (ABS), polyethylene, polypropylene, or the like. The needle can be a surgical grade stainless steel. Other materials and methods of manufacture known to those of ordinary skill in the art of medication pen technology may be adapted for use herein without departing from the scope of the invention. To assemble the parts, the hub assembly may be constructed with the needle separately, with adhesive applied in the interface area to secure the cannula to the hub, and this sub-assembly may then be assembled with the other components.

The foregoing description of the preferred embodiments is not to be deemed limiting of the invention, which is defined by the following claims. The foregoing description should provide the artisan of ordinary skill with sufficient information to practice variants of the embodiments described. Features and improvements described in dependent claims or in connection with one embodiment may be combined with those of another independent claim or another embodiment, provided they are not inconsistent therewith, without departing from the scope of the invention.

The invention claimed is:

1. A pen needle, comprising
    a hub having a distal end, and a proximal end for attachment to a delivery device;
    a needle coupled to said hub and having a distal end extending from said distal end of said hub and a proximal end extending proximally relative to said hub for connecting to the delivery device;
    a distal needle shield coupled to said hub for sliding between a first extended position to shield said distal end of said needle, a retracted position to expose said distal end of said needle for injecting a substance into a patient, and a second extended position to shield said distal end of said needle; and
    a proximal needle shield coupled to said hub for sliding from a retracted position where said proximal end of said needle is exposed to an extended position, said proximal needle shield coupled to said distal needle shield for retaining said proximal needle shield in the retracted position, wherein said distal needle shield is rotatable by axial movement relative to said hub from the first position to the second position to disconnect said distal needle shield from said proximal needle shield.

2. The pen needle of claim 1, further comprising a spring having a first end for biasing said distal needle shield to the extended position and a second end for biasing said proximal needle shield to the extended position.

3. The pen needle of claim 2, wherein said first end of said spring contacts a proximal end of said distal needle shield, and said second end contacts a base of said proximal needle shield.

4. The pen needle of claim 1, wherein said distal needle shield has a distal end, a proximal end, and at least one coupling member at said proximal end configured for coupling with said proximal needle shield.

5. The pen needle of claim 4, wherein said proximal needle shield has a coupling member releasably coupled to said coupling member of said distal needle shield when said distal needle shield is in the first extended position and said proximal needle shield is in the retracted position.

6. The pen needle of claim 5, further comprising a spring extending between said distal needle shield and said proximal needle shield, and where said spring is in a compressed state when said distal needle shield is coupled to said proximal needle shield.

7. The pen needle of claim 6, wherein said spring is in an extended state when said distal needle shield is in the extended position and said proximal needle shield is in the extended position.

8. The pen needle of claim 5, wherein said distal needle shield is configured to rotate relative to said hub by axial movement to the retracted position, and where rotation of said distal needle shield disengages said coupling member of said distal needle shield from said coupling member of said proximal needle shield.

9. The pen needle of claim 8, wherein said hub has a sidewall and an inner wall oriented transversely to an axis of said hub and spaced between said distal end and said proximal end of said hub, and where said inner wall has an opening configured to receive an end of said proximal needle shield.

10. The pen needle of claim 9, wherein said proximal needle shield has a base oriented on a distal side of said inner wall, and a shield member oriented to extend through said opening in said inner wall when said proximal needle shield moves to the extended position, and where said shield member has an axial length to shield said proximal end of said needle.

11. The pen needle of claim 8, wherein said inner surface of said hub has a rotation mechanism to rotate said distal needle shield when said distal needle shield moves toward said distal end of said hub.

12. The pen needle of claim 10, wherein said inner wall has a plurality of openings spaced around said proximal end of said needle, and where said base of said proximal needle shield has a plurality of said shield members extending through a respective opening in said inner wall, and where said shield members have an axial length to shield said proximal end of said needle.

13. The pen needle of claim 12, wherein said inner wall of said hub comprises a post extending toward said distal end of said hub, and where said base of said proximal needle shield has an opening configured for sliding axially on said post.

14. The pen needle of claim 1, wherein said proximal needle shield comprises a plurality of coupling members extending from a distal side of a base of said proximal needle shield, and where said distal needle shield includes a plurality of coupling members configured for coupling with a respective coupling member of said proximal needle shield.

15. The pen needle of claim 14, wherein said coupling members of said distal needle shield include a coupling tab, and where said coupling members of said proximal needle shield include a coupling tab for coupling with a respective coupling tab of said distal needle shield to retain said proximal needle shield in the retracted position.

16. The pen needle of claim 15, wherein said distal needle shield comprises a projection configured to engage a detent on said hub when said distal needle shield is in the first extended position, and where said projection on said distal needle shield engages said detent on said hub to rotate said distal needle shield when said distal needle shield moves toward said proximal end of said hub to separate said coupling tab of said distal needle shield from said coupling tab of said proximal needle shield.

17. The pen needle of claim 16, wherein said projection on said distal needle shield comprises a cam surface and where said detent on said hub comprises a cam surface, whereby axial movement of said distal needle shield relative to said hub causes rotation of said distal needle shield relative to said hub to separate said distal needle shield from said proximal needle shield.

18. The pen needle of claim 17, wherein said projection on said distal needle shield projects radially outward relative to an axis of said distal needle shield, and where said detent on said hub projects radially inward.

19. The pen needle of claim 18, where said distal needle shield comprises a locking member to lock said distal needle shield second extended position, and where said side wall comprises a locking member to lock said proximal needle shield in the extended position.

20. The pen needle of claim 1, wherein said hub has a sidewall and an inner wall extending transversely relative to said sidewall with an opening, and where said proximal needle shield extends through said opening in said inner wall, said proximal needle shield having a distal end on a first side of said inner wall for engaging a biasing member, and a proximal end on a second side of said inner wall for shielding said proximal end of said needle.

21. A pen needle, comprising
a hub having a sidewall, an inner wall extending transversely relative to said side wall, a proximal end for attachment to a delivery device, and a distal end;
a needle coupled to said hub and having a distal end extending from said distal end of said hub and a proximal end at a proximal end of said hub;
a distal needle shield coupled to said hub for sliding with respect to said hub between a first extended position to shield said distal end of said needle, a retracted position to expose said distal end of said needle, and a second extended position to shield the distal end of the needle, said distal needle shield having a first coupling member;
a proximal needle shield at the proximal end of the hub and having a base on a distal side of inner wall, and a shield member extending toward said proximal end of said hub through an opening in said inner wall of said hub, said proximal needle shield being movable from a retracted position where said proximal end of said needle is exposed and an extended position relative to said proximal end of said needle, said proximal needle shield having a second coupling member configured for coupling to said first coupling member of said distal needle shield and retaining said proximal needle shield in the retracted position; and
a spring having a first end contacting said distal needle shield for biasing said distal needle shield in a distal direction to the second extended position, and a second end contacting said base of said proximal needle shield for biasing said proximal needle shield and said shield member to the extended position.

22. The pen needle of claim 21, wherein said spring is in a compressed state when said distal needle shield is coupled to said proximal needle shield.

23. The pen needle of claim 21, wherein said distal needle shield is configured to rotate relative to said hub by axial movement of said distal needle shield toward said proximal end of said hub to separate said first coupling member from said second coupling member.

24. The pen needle of claim 23, wherein said distal needle shield has a projection and said side wall of said hub has a detent configured to engage said projection on said distal needle shield to retain said distal needle shield in the first extended position and rotate said distal needle shield by axial movement of said distal needle shield.

25. The pen needle of claim 24, wherein said first coupling member comprises a first coupling tab and said second coupling member comprises a second coupling tab configured for removably coupling to said first coupling tab.

26. The pen needle of claim 25, wherein said proximal needle shield has a plurality of shield members extending from a proximal side of said base, said shield members configured for extending through openings in said inner wall when said proximal needle shield is in the extended position, and where said shield members surround a tip of said proximal end of said needle.

* * * * *